(12) United States Patent
Tata et al.

(10) Patent No.: US 12,295,719 B2
(45) Date of Patent: May 13, 2025

(54) ENDOSCOPE NAVIGATION SYSTEM WITH UPDATING ANATOMY MODEL

(71) Applicant: COVIDIEN LP, Mansfield, MA (US)

(72) Inventors: Derek Scot Tata, Loveland, CO (US); Peter Douglas Colin Inglis, Boulder, CO (US); Alexandra R. Hause, Denver, CO (US)

(73) Assignee: Covidien LP, Mansfield, MA (US)

( * ) Notice: Subject to any disclaimer, the term of this patent is extended or adjusted under 35 U.S.C. 154(b) by 165 days.

(21) Appl. No.: 17/719,007

(22) Filed: Apr. 12, 2022

(65) Prior Publication Data

US 2022/0354380 A1    Nov. 10, 2022

Related U.S. Application Data

(60) Provisional application No. 63/185,186, filed on May 6, 2021.

(51) Int. Cl.
*A61B 5/06*    (2006.01)
*A61B 1/00*    (2006.01)
(Continued)

(52) U.S. Cl.
CPC .......... *A61B 5/066* (2013.01); *A61B 1/00009* (2013.01); *A61B 1/00016* (2013.01); *A61B 1/0005* (2013.01); *A61B 1/0051* (2013.01); *A61B 1/05* (2013.01); *A61B 1/2676* (2013.01); *G06T 7/33* (2017.01); *G06T 7/75* (2017.01); *G06T 19/003* (2013.01); *G06T 19/20* (2013.01); *G16H 30/40* (2018.01); *G16H 50/50* (2018.01); *G06T 2207/10068* (2013.01); *G06T 2207/10081* (2013.01); *G06T 2207/10088* (2013.01); *G06T 2219/2004* (2013.01); *G06T 2219/2016* (2013.01)

(58) Field of Classification Search
None
See application file for complete search history.

(56) References Cited

U.S. PATENT DOCUMENTS 8,116,847 B2 * 2/2012 Gattani ................. A61B 34/20
378/4
8,194,122 B2   6/2012 Amling et al.
(Continued)

FOREIGN PATENT DOCUMENTS

EP    2433553 A1    3/2012
JP    2014210085 A   11/2014
(Continued)

OTHER PUBLICATIONS

SiMMS Imperial, "NOViSE—Augmented Reality Support", Feb. 11, 2020, URL: https://www.youtube.com/watch?v=Mq2FFUXSXfY (Year: 2020).*

(Continued)

*Primary Examiner* — David H Chu

(57) ABSTRACT

An endoscope navigation system is provided that updates an anatomy model based on a live camera signal. As the endoscope advances within the patient, a camera signal, and corresponding position signal, of the endoscope, is provided and used to update the anatomy model based on identified divergences between the camera signal at a particular position and anatomy model.

18 Claims, 11 Drawing Sheets

(51) Int. Cl.
*A61B 1/005* (2006.01)
*A61B 1/05* (2006.01)
*A61B 1/267* (2006.01)
*G06T 7/33* (2017.01)
*G06T 7/73* (2017.01)
*G06T 19/00* (2011.01)
*G06T 19/20* (2011.01)
*G16H 30/40* (2018.01)
*G16H 50/50* (2018.01)

(56) References Cited

U.S. PATENT DOCUMENTS

| | | |
|---|---|---|
| 8,652,033 B2 | 2/2014 | Berci et al. |
| 8,715,172 B1 | 5/2014 | Girgis |
| 8,746,239 B2 | 6/2014 | Yoshida |
| 8,827,899 B2 | 9/2014 | Farr et al. |
| 8,982,199 B2 | 3/2015 | Amling et al. |
| 9,123,155 B2 | 9/2015 | Cunningham et al. |
| 9,498,112 B1 | 11/2016 | Stewart et al. |
| 9,538,908 B2 | 1/2017 | Allyn et al. |
| 9,687,141 B2 | 6/2017 | McGrath |
| 9,820,641 B2 | 11/2017 | McGrath |
| 10,010,379 B1 | 7/2018 | Gibby et al. |
| 10,149,957 B2 | 12/2018 | Runnels |
| 2007/0197896 A1 | 8/2007 | Moll et al. |
| 2007/0236514 A1 | 10/2007 | Agusanto et al. |
| 2008/0177146 A1 | 7/2008 | Chen |
| 2008/0177148 A1 | 7/2008 | Chen et al. |
| 2008/0312507 A1 | 12/2008 | Kim |
| 2011/0130632 A1 | 6/2011 | McGrail et al. |
| 2011/0137127 A1 | 6/2011 | Schwartz |
| 2011/0245609 A1 | 10/2011 | Laser |
| 2012/0157834 A1* | 6/2012 | Lazebnik ............... A61B 34/25 600/437 |
| 2012/0294498 A1* | 11/2012 | Popovic ............... A61B 1/0005 382/128 |
| 2013/0057667 A1 | 3/2013 | McGrath |
| 2013/0267838 A1 | 10/2013 | Fronk et al. |
| 2014/0031700 A1 | 1/2014 | Ferrantelli |
| 2014/0160261 A1 | 6/2014 | Miller et al. |
| 2014/0275760 A1 | 9/2014 | Lee et al. |
| 2014/0378763 A1 | 12/2014 | Atarot |
| 2015/0031990 A1* | 1/2015 | Boctor ............... A61B 8/483 600/440 |
| 2016/0199009 A1 | 7/2016 | Gilboa |
| 2016/0242627 A1* | 8/2016 | Takahashi ........... A61B 1/0615 |
| 2016/0279365 A1 | 9/2016 | Esnouf |
| 2017/0055809 A1 | 3/2017 | Omoto |
| 2017/0209071 A1* | 7/2017 | Zhao ....................... A61B 5/06 |
| 2018/0132944 A1* | 5/2018 | Yan ........................ G06T 7/74 |
| 2018/0193102 A1 | 7/2018 | Inoue |
| 2018/0292199 A1 | 10/2018 | Tojo |
| 2018/0296281 A1 | 10/2018 | Yeung et al. |
| 2018/0324352 A1 | 11/2018 | Furuhata |
| 2019/0046417 A1* | 2/2019 | Flexman ............. A61J 15/0088 |
| 2019/0133430 A1 | 5/2019 | Inglis et al. |
| 2019/0328465 A1* | 10/2019 | Li .......................... G06T 7/0012 |
| 2020/0138404 A1* | 5/2020 | Goodman .............. G16H 50/20 |
| 2020/0195903 A1* | 6/2020 | Komp .................... H04N 13/25 |
| 2020/0254204 A1 | 8/2020 | Moffat et al. |
| 2021/0196398 A1* | 7/2021 | Ye .......................... A61B 1/307 |
| 2021/0196425 A1* | 7/2021 | Shelton, IV ......... A61B 1/0016 |
| 2021/0353149 A1* | 11/2021 | Abbosh ................ G06T 7/0012 |

FOREIGN PATENT DOCUMENTS

| | | |
|---|---|---|
| WO | 2020/005890 A1 | 1/2020 |
| WO | 2022/133248 A1 | 6/2022 |
| WO | 2022/266500 A1 | 12/2022 |

OTHER PUBLICATIONS

International Written Opinion for the International Application No. PCT/IB2022/054037 mailed Jul. 27, 2022 (8 pages).

International Search Report for the International Application No. PCT/IB2022/054037 mailed Jul. 27, 2022 (6 pages).

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Bowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319. http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS One | https://doi.org/10.1371/journal.pone.0186691 (Nov. 3, 2017).

Ambu_aScope_3_Large_Brochure_4963605 (Oct. 2017).

International Search Report and Written Opinion for PCT Application PCT/GB2018/053300 dated Feb. 20, 2019; 15 pgs.

International Search Report and Written Opinion for PCT/US2020/051734 dated May 14, 2020; 11 pgs.

PCT Invitation to Pay Fees, PCT Application No. PCT/EP2020/073196, mailed Nov. 16, 2020.

* cited by examiner

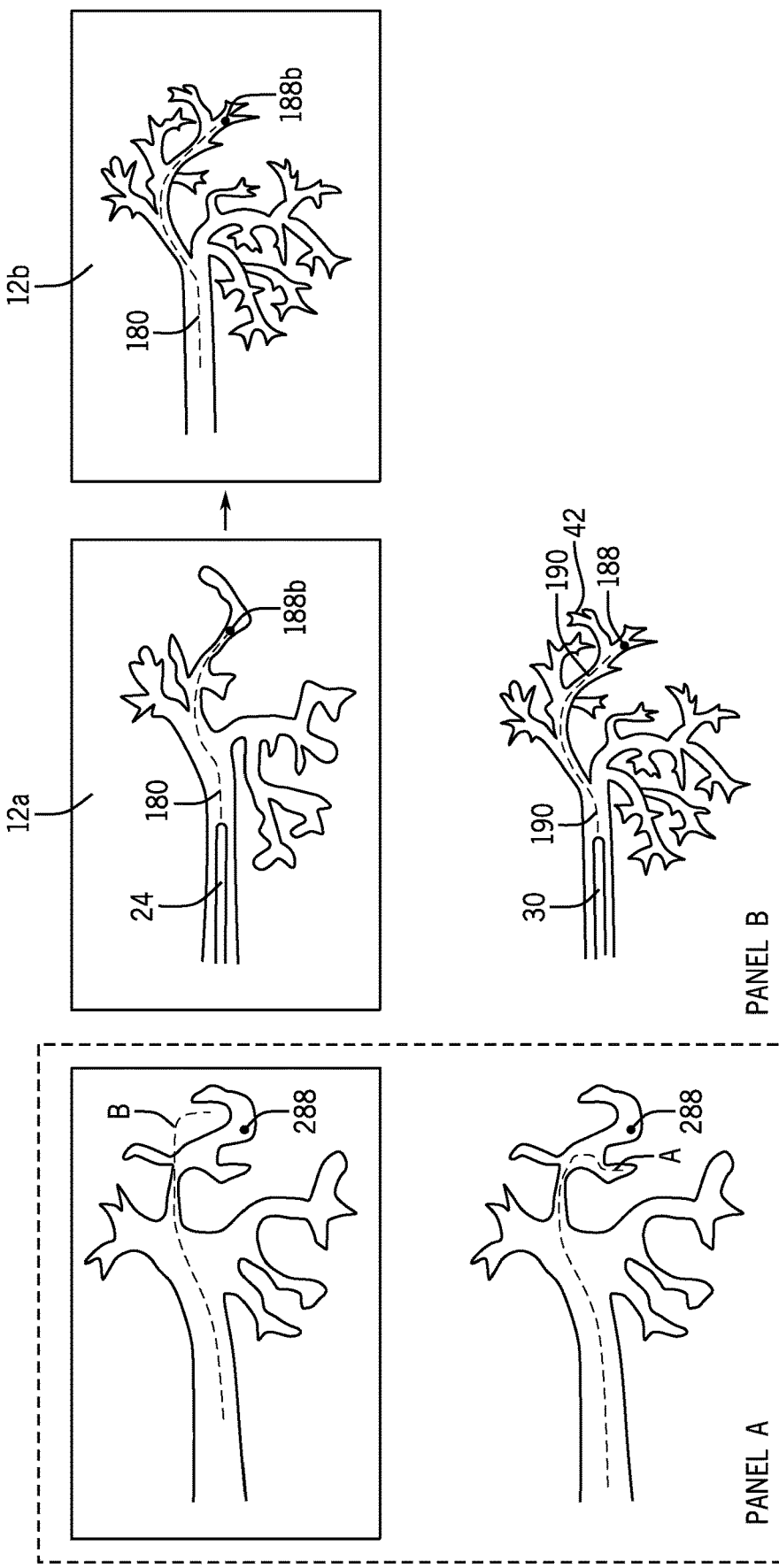

ENDOSCOPE NAVIGATION SYSTEM WITH UPDATING ANATOMY MODEL

CROSS-REFERENCE TO RELATED APPLICATIONS

This application claims the benefit of U.S. Provisional Application No. 63/185,186 filed May 6, 2021, entitled "ENDOSCOPE NAVIGATION SYSTEM WITH UPDATING ANATOMY MODEL," which is incorporated herein by reference in its entirety.

BACKGROUND

The present disclosure relates generally to medical devices and, more particularly, to endoscope navigation techniques that use endoscope images acquired during a patient procedure to update or correct a patient anatomy model, and related methods and systems.

Medical endoscopes are long, flexible instruments that can be introduced into a cavity of a patient during a medical procedure in a variety of situations to facilitate visualization and/or medical procedures within the cavity. For example, one type of scope is an endoscope with a camera at its distal end. The endoscope can be inserted into a patient's mouth, throat, trachea, esophagus, or other cavity to help visualize anatomical structures, or to facilitate procedures such as biopsies or ablations. The endoscope may include a steerable distal tip that can be actively controlled to bend or turn the distal tip in a desired direction, to obtain a desired view or to navigate through anatomy.

The position and arrangement of airway passages or other cavities is variable between patients. Thus, to assist in endoscope navigation, a model or estimation of the patient anatomy can be created prior to a procedure for an individual patient using computer tomography (CT) images or magnetic resonance imaging (MRI). However, in certain cases, the patient's anatomy may diverge from the model, e.g., based on patient condition changes that have occurred after the model was created or inaccuracies in the model or real-time movements of the patient during a procedure. Accordingly, navigation using the model may not yield desired positioning of the endoscope in the patient.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, an endoscope navigation system is provided that includes an endoscope having a steerable distal tip. The distal tip includes a camera producing an image signal and a position sensor producing a position signal indicative of a position of the distal tip. The endoscope navigation system also includes a graphics controller that is programmed with instructions to render a modeled navigation path in an anatomy model of a patient1; receive the image signal and the position signal; identify a divergence between an anatomy model and the image signal; and update the anatomy model based on the identified divergence. The endoscope navigation system also includes display screen displaying the updated anatomy model.

In an embodiment, an endoscope navigation method includes displaying an anatomy model of a patient on a display screen; receiving an image signal and a position signal from an endoscope, the position signal indicative of a position of a distal tip of the endoscope during navigation; rendering a graphical marker at a location in the displayed anatomy model that corresponds to the position of the distal tip within the patient; identifying a divergence between image signal and the location of the graphical marker; and updating the anatomy model based on the identified divergence.

In an embodiment, a graphics controller of an endoscope navigation system includes a wireless receiver that receives an image signal and a position signal from an endoscope. The graphics controller also includes a processor executing instructions stored in a memory that cause the processor to generate an initial anatomy model from patient scan data; provide the initial anatomy model to a display; update the initial anatomy model based on the image signal to generate an updated anatomy model; and provide the updated anatomy model to the display.

In an embodiment, an endoscope navigation method includes displaying an anatomy model of a patient on a display; receiving a first image signal and a position signal from an endoscope; determining that additional images are required to validate a portion of the anatomy model corresponding to the position signal; transmitting instructions to the endoscope to cause the endoscope to display a notification to capture additional images at or near a position of the image signal; receiving a second image signal comprising the additional captured images; and updating the anatomy model based on the second image signal.

In an embodiment, a method for closed loop navigation through an anatomy model is provided that includes the steps of receiving an image signal comprising image data from a camera at a distal end of an endoscope; rendering a position marker in an anatomy model at a location corresponding to the distal end of the endoscope; displaying a navigation path in the anatomy model from the position marker to a target location in the anatomical model; moving the position marker in the anatomy model according to movement of the endoscope; updating the anatomy model based on an identified divergence between the anatomy model and the image data; and displaying the navigation path in the updated anatomy model.

Features in one aspect or embodiment may be applied as features in any other aspect or embodiment, in any appropriate combination. For example, features of a system, handle, controller, processor, scope, method, or component may be implemented in one or more other system, handle, controller, processor, scope, method, or component.

BRIEF DESCRIPTION OF THE DRAWINGS

Advantages of the disclosed techniques may become apparent upon reading the following detailed description and upon reference to the drawings in which:

FIG. 7 is a view showing example anatomy model updating, according to an embodiment of the disclosure.

DETAILED DESCRIPTION OF SPECIFIC EMBODIMENTS

Figure 1:
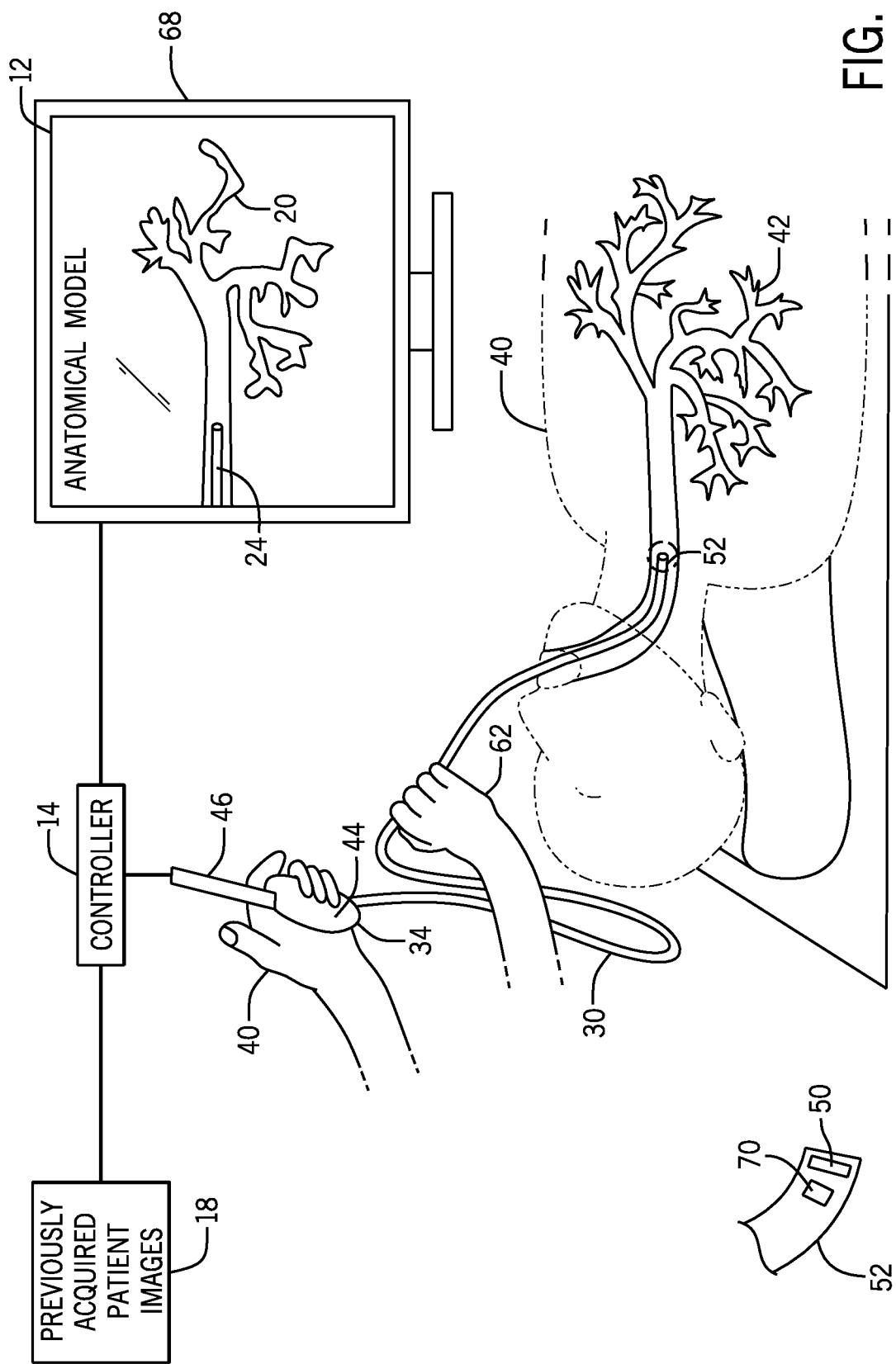
FIG. 1 is a view of an endoscope navigation system including an anatomy model of a patient, according to an embodiment of the disclosure.

A medical scope or endoscope as provided herein is a thin, elongated, flexible instrument that can be inserted into a body cavity for exploration, imaging, biopsy, or other clinical treatments, including catheters, narrow tubular instruments, or other types of scopes or probes. Endoscopes may be navigated into the body cavity (such as a patient's airway, gastrointestinal tract, oral or nasal cavity, or other cavities or openings) via advancement of the distal end to a desired position and, in certain embodiments, via active steering of the distal end of the endoscope. Endoscopes may be tubular in shape.

Advancement of long, flexible medical devices into patient cavities is typically via force transferred from a proximal portion of the device (outside of the patient cavity), that results in advancement of the distal tip within the patient cavity. As used herein, "proximal" refers to the direction out of the patient cavity, back toward the handle end of a device, and "distal" refers to the direction forward into the patient cavity, away from the doctor or caregiver, toward the probe or tip end of the device. For example, a doctor or other caregiver holding a proximal portion of the endoscope outside of the patient cavity pushes downward or forward, and the resulting motion is transferred to the distal tip of the endoscope, causing the tip to move forward (distally) within the cavity. Similarly, a pulling force applied by the caregiver at the proximal portion may result in retreat of the distal tip or movement in an opposing (proximal) direction out of the patient cavity. The endoscope can also include steering controls to change orientation at the distal end based on operator input to navigate or point the endoscope in a desired direction.

Because patient cavities are not regularly shaped or sized, the endoscope procedure may include navigation through an unpredictable and tortuous path to reach a particular point in the anatomy (such as reaching into branches of the lungs). Endoscopes that have a camera at the distal tip provide an image view from the distal tip during steering. However, based on the image view alone, it may be difficult for the doctor, or any caregiver in the room, to know where the endoscope is positioned within the patient anatomy, how far it has moved proximally or distally, what path it has taken through the patient anatomy, and what obstacles or anatomical landmarks are beyond the camera view. For example, it can be difficult to determine which branch of a patient's lungs is the correct path to choose, and correcting wrong turns often involves backtracking to a familiar landmark, such as a carina, and starting over. This back-tracking and re-tracing of navigation through a patient's airway (or other cavity) lengthens the duration of the clinical procedure, which can increase the risk of a poor outcome for the patient as well as costs for the healthcare provider.

Accordingly, it is beneficial to provide a patient-specific or, in some cases, a general or generic patient model representative of an average patient anatomy (which may be selected from an available set of models based on patient demographic, size, age, gender, etc.) of the anatomy that can be used for endoscope navigation to help locate the endoscope within the patient. In an embodiment, the model is displayed together with a graphical marker that simulates the progress of an endoscope and/or other tool as it is moved through the patient anatomy during the clinical procedure, to provide additional context to the endoscope view. However, the accuracy of the anatomy model may be compromised by the resolution of data used to generate the model, patient movement (such as coughing, breathing, stretching) or repositioning during the procedure, or changes in clinical condition of the patient relative to the time the anatomy model images were collected, by way of example. Various embodiments of an endoscope navigation system with real-time updating of patient-specific anatomy model using live, real-time camera data to account for patient movement or correct the anatomy model and provide more accurate navigation information are described below.

An example endoscope navigation system 10 including an anatomy model 12 that may be updated according to the disclosed embodiments is illustrated in FIG. 1. The anatomy model 12 can be created in various different ways, such as using previously acquired images 18 or anatomical data from the patient. In an embodiment, the model 12 is created from a scan of the patient prior to an endoscopy procedure. The scan can be CT (computed tomography), MRI (magnetic resonance imaging), x-ray, or other diagnostic or imaging scans. These scans can be used to build a three-dimensional model of the actual anatomy of an individual patient. For example, computations from a CT scan can be used to build a three-dimensional model of a patient's airways (for example, computer-based methods for segmentation of anatomy based on CT scans). The resulting three-dimensional model shows the actual unique airway branches of that individual patient, as the airways split and branch out below the left and right bronchial tubes.

In FIG. 1, the anatomy of the model 12 is the patient's airways, but it should be understood that other anatomy models can be used in other procedures and contexts, including for example models of the skeleton, soft tissue, gastrointestinal structures, or others. The anatomy model 12 can be a simplified model generated from rich image data. That is, the overall anatomy model can be a cartoon view, line drawing, three-dimensional model, or section view of the airways. The anatomy model 12 can be rendered to show the approximate locations and dimensions of airway passages and surrounding tissue walls, such as the tracheal or bronchial walls. For example, using CT scan data including density information, the anatomy model 12 can be generated based on density rules to designate less dense areas as likely to be open airway passages and more dense areas as likely to be tissue. Airway walls of the anatomy model are rendered based on tissue areas located at the border of open airway passages. In such an example, the tissue walls can be designated in the anatomy model 12 with or without fine feature resolution or texturing. The anatomy model 12 can be generated by or an updated by the system 10 as provided herein.

The anatomy model 12 may be displayed on a display screen 68 as computer-generated graphics 20 during an endoscope procedure. The computer-generated graphics 20 may also include a simulated endoscope 24 tracking progress of a real-world endoscope 30 in real time. The simulated endoscope 24 is a computer-generated animation that represents the actual endoscope 30 that is being moved within the patient 40.

The simulated endoscope 24 tracks real-world movement of the endoscope 30 caused by operator manipulation in a distal or proximal direction and/or orientation changes mediated by operator steering inputs to an endoscope controller 34. The graphics controller 14 renders the simulated endoscope 24 within the anatomy model 12, and moves the simulated endoscope 24 within the model 12 in coordination with movements of the real-world endoscope 30. The position of the simulated endoscope 24 within the model 12 represents the actual position, which may include an orientation or pose, of the real-world endoscope 30 within the patient 40. Thus, when the endoscope operator advances the endoscope 30 distally within the patient, the graphics controller 14 adjusts the rendering of the simulated endoscope 24 to move it a corresponding distance through the model 12. The simulated endoscope 24 is the marker showing the live, real-time, moving position of the endoscope 30 within the global map of the model 12 in a manner similar to graphical markers of a vehicle navigating through a street map.

The endoscope 30 is inserted into a patient 40 during a clinical procedure to navigate within a patient cavity, illustrated by way of example as patient airway passages 42. The interior patient airway passages 42 shown in FIG. 1 are the real-world, live patient anatomy. The endoscope 30 is an elongated, tubular scope that is connected at its proximal end to the endoscope controller 34. The endoscope controller 34 includes a handle, puck, or wand 44 with a display screen 46. The display screen 46 shows live or real-time images from a camera 50 at the distal tip 52 of the endoscope 30, within the patient airway passages 42. The clinician who is operating the endoscope (the operator) holds the handle 44 with his or her left hand 60, and grips or pinches the endoscope 30 with his or her right hand 62. The operator can move the endoscope 30 proximally or distally with the right hand, to advance the endoscope forward (distally) into the patient or withdraw it back (proximally), while watching the resulting images from the camera on the display screen 46.

In an embodiment, the display screen 46 is a touch screen, and the operator can input touch inputs on the screen 46 (such as with the operator's left thumb) to steer the distal tip 52 of the endoscope 30, such as to bend it right, left, up, or down. In this example, the operator is using their right hand 62 to move the endoscope forward into the patient's lungs, using their left thumb 60 to steer the distal tip 52 to navigate and adjust the camera's view, and watching the resulting live camera view of the lungs, bronchial tubes, or other features of the airway passages 42 on the display screen 46.

In an embodiment, the display screen 46 is small and compact so that it can be battery-powered, lightweight, and hand-held by the operator holding the handle 44. The screen 46 may also be small so that the operator can keep a clear view of the patient 40 as well as the screen 46, in the same line of sight. However, another clinician or caregiver in the room may have difficulty seeing the camera images on the display screen 46. Further, the camera view may not provide sufficient context to track progress of the distal tip 52 within the airway passages 42. Thus, the anatomy model 12 may be displayed on a separate display screen 68 (such as a larger display screen mounted on the wall or pedestal or other mount for visibility within the room), and the operator and other caregivers can monitor the progress of the simulated endoscope graphical marker 24 within the anatomy model 12. For example, the screen 68 may be a tablet, mobile device, laptop, monitor, screen, or other display to show the real-time location of the endoscope 30 within the modeled patient anatomy 12.

The real-time location of the endoscope 30 can be provided by a position sensor 70 located at the distal tip 52. The camera 50 and the position sensor 70 capture live signals during an endoscopy procedure that are provided in substantially real-time to the controller 14 via communication between the endoscope 30 and the controller 14. In an embodiment, the camera 50 is positioned at the terminus of the distal tip 52 of the endoscope 30, to obtain a clear view forward or in a distal direction. The position sensor 70 is located just behind the camera 50, so that position data, which may include orientation data or pose information, from the sensor 70 is representative of the position and orientation of the camera 50. In an embodiment, the position sensor 70 is adjacent to the camera 50. In an embodiment, the position sensor 70 is mounted on a flex circuit behind the camera 50. In an embodiment, the position sensor 70 is mounted on the same flex circuit as the camera 50, though the position sensor 70 and the camera 50 may or may not be in communication on the shared flex circuit. In an embodiment, the position sensor 70 has a size of between 1-2 mm in each dimension. In an embodiment, the camera 50 has a size of between 1-2 mm in each dimension.

As the real-world position of the distal tip 52 changes, the position sensor 70 provides updated position signals to the system 10, which in turn are used by the graphics controller 14 to move the simulated endoscope relative to the model 12. Accordingly, as the endoscope 30 moves, image signals from the camera 50 are indicative of changing anatomical features and the position signals from the position sensor 70 are indicative of corresponding changes in absolute position and orientation of the distal tip 52 in space. Additionally, the rendering of the simulated endoscope 24 within the anatomy model 12 can be set based on the live image signal from the endoscope 30. The system 10, using image processing, can identify landmarks in the live image signal and correlate the identified landmarks to corresponding features in the anatomy model 12.

However, the anatomy model 12 may not fully align with the live patient anatomy. In some instances, such inaccuracies may result in the real-world airway passages 42 being slightly shifted, stretched, or changed relative to the corresponding locations in the model 12. Even a model 12 that is initially correctly aligned to the patient 40 may become less accurate over the course of a clinical procedure due to patient movement, position shifts, or changes in health status. Further, the generated model 12 may include inherent inaccuracies in size, scale, or presence/absence of anatomical features based on the resolution limits of the imaging technology or patient-specific variables that influence image quality. In another example, inaccuracies in the anatomy model 12 may be based on patient position differences used in scanning versus endoscopy. For example, CT images used to generate the anatomy model 12 can be acquired with the patient's arms positioned above their head and with the patient holding in a full breath. In contrast, patients undergoing endoscopy generally are arranged with their arms by their sides and breathing independently or via intubation and mechanical ventilation. Such differences in patient positioning and breathing may cause associated position shifts in the airway passages 42, rendering the anatomy model 12 at least partly inaccurate. While these inaccuracies may be on a millimeter scale and may only be within discrete regions of the model 12, such differences may result in steering difficulties when the operator is using the anatomy model 12 to navigate, and the expected anatomy based on the anatomy model conflicts with the actual live view through the endoscope camera 50.

As provided herein, the endoscope navigation system 10 incorporates real-time signals from the camera 50 and the position sensor 70 to update the anatomy model 12 based on the local conditions captured by the camera 50 and position data captured by the position sensor 70. The updating may include correcting portions of the anatomy model 12, adjusting a scale of the anatomy model 12, changing relationships between features of the anatomy model 12 (such as stretching or compressing portions of the model), and/or adjusting the rendering of the simulated endoscope 24 within the anatomy model 12 by way of example. The updating may also include rerouting of suggested navigation routes from the simulated endoscope 24 to a desired destination based on the updated anatomy model 12. Notably, in an embodiment, the rendering of the simulated endoscope 24 is updated in the model without changing the dimensions or characteristics of the model itself. For example, if the anatomy model 12 differs from the live patient physiology in a particular way (such that the actual endoscope 30 has reached a particular feature in the patient, but the simulated endoscope 24 hasn't reached that feature yet in the model 12), the simulated endoscope 24 can be moved within the model 12 to correspond to the position of the endoscope 30 in the patient (such as by moving the simulated endoscope 24 within the model 12 to the feature). In this way, in order to provide accurate navigation to the user, the simulated endoscope 24 can be moved to track the live endoscope without actually changing the model 12 itself. Thus, in an embodiment, updating the model includes updating the placement, orientation, or movement of the simulated endoscope 24 within the model.

Thus, the system 10 transforms a pre-existing static anatomy model into a dynamic map that is adjusted based on live, real-time data from the endoscope 30. As the endoscope 30 progresses through the airway passages 42, the acquired data from the camera 50 and position data from the position sensor 70 are used to update the anatomy model 12. The anatomy model 12 becomes more accurate to the live patient as the endoscope 30 advances within the airway passages 42 after each successive update. The live data from the patient 40 captured by the endoscope 30 serves as the ground truth in the endoscope navigation system 10, and supplants older or less accurate data in the anatomy model 12. In an embodiment, when the anatomy based on the endoscope camera 50 and the anatomy model 12 diverge, the data from the endoscope camera 50 governs the updating. Once updated, the changes are included in the displayed anatomy model 12 and may include position shifts of features of the model 12. The rendering of the simulated endoscope 24 can be updated in the model 12 based on the relative position changes.

Figure 2:
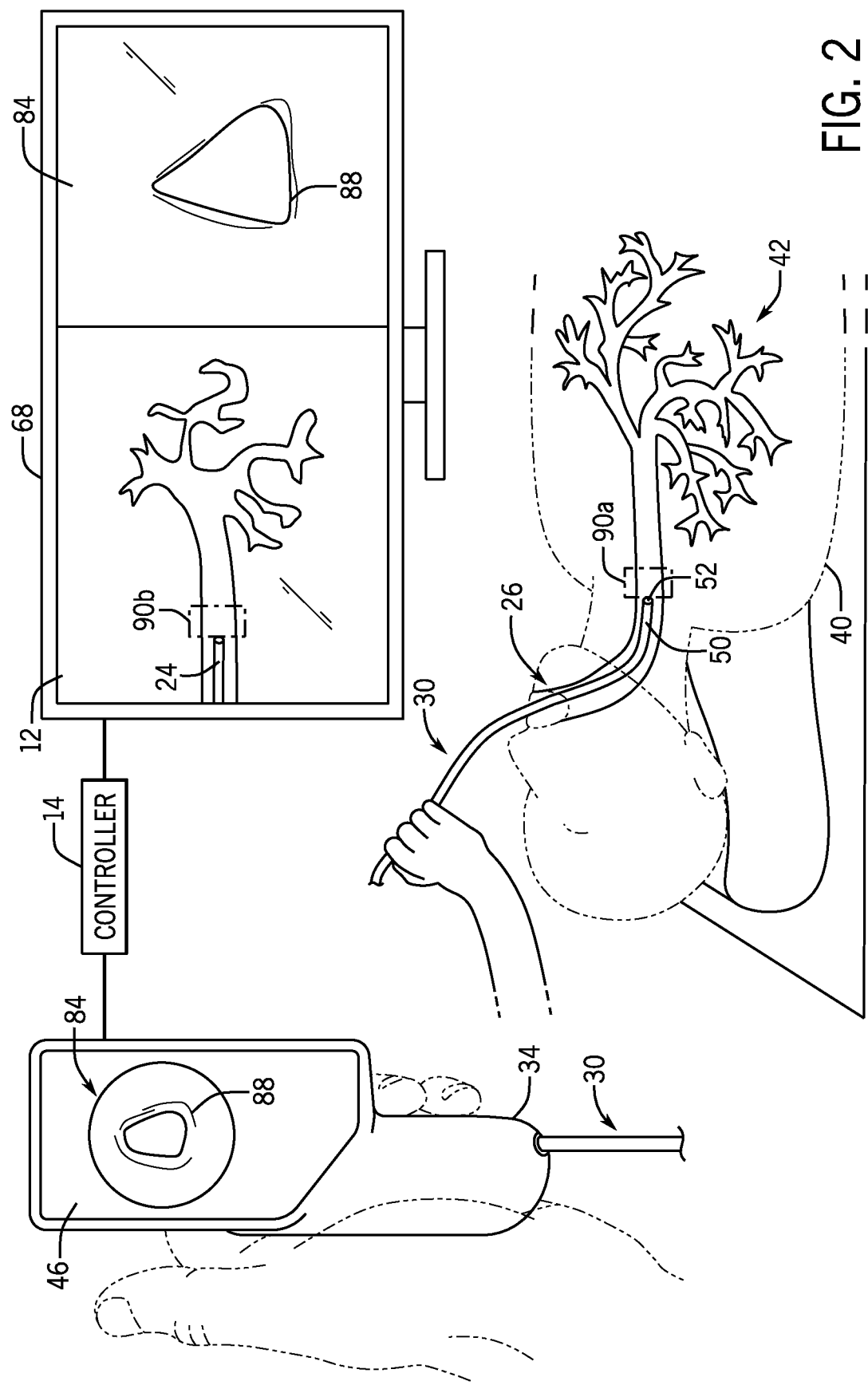
FIG. 2 is an endoscope navigation system including an endoscope view of vocal cords captured by the endoscope camera, according to an embodiment of the disclosure.

In an embodiment, the endoscope navigation system 10 includes iterative updating of the anatomy model 12 during an endoscope procedure. FIG. 2 is a system view including an example live endoscope image 84 representing a current, real-time video feed from the camera 50 at the distal tip 52 of the endoscope 30 during the clinical procedure. The live camera image 84 is provided to the endoscope controller 34, which passes the image signal (and/or associated position data) to the graphics controller 14. If the controller 14 identifies a divergence between the model 12 and the image (and/or position) signals, the model 12 is updated. The image data at a particular location of the distal tip 52 is confined to the field of view of the camera 50. As illustrated, the camera 50 captures data from a region 90a in the patient anatomy correlated to a region 90b in the model 12.

The image 84 shown on the operator display screen 46 is also displayed on the separate display screen 68. As the patient condition changes and/or the endoscope steers or moves, the image 84 shows the current view from the endoscope camera 50. In the illustrated embodiment, the endoscope image 84 shows an image of patient vocal cords, and the separate display screen 68 displays a side-by-side view of the image 84 and the anatomy model 12. The simulated endoscope 24 is positioned at a location generally corresponding to the vocal cord region of the model 12. In an embodiment, the separate display screen 68 shows both the anatomy model 12 and the endoscope image 84 on different portions of the display. The display may toggle between these two different views.

The rendering of the simulated endoscope 24 within the model 12 can be based on the stream of live endoscope data and updated in real time. For example, the stream of live endoscope data is used to correct any relative position inaccuracies and to account for patient position shifts over the course of the procedure. This correction to the model 12 can be done without relying on patient position sensors within the room. The model 12 is updated and synchronized to the actual live image data coming from the endoscope, regardless of how the patient is oriented in the room. Rather than using an active patient sensing device, such as an electromagnetic sensing pad underneath the patient 40, patient movement can be accounted for based on the synchronization between the patient and the model 12.

Conventional magnetic navigation systems, such as those including an electromagnetic sensing pad, place the patient in a global reference frame, then track endoscope position in that global reference frame. The global reference frame may be contrasted with a patient reference frame and/or an endoscope reference frame. As the patient frame is dynamic for the reasons listed above, this leads to inaccuracies over time. In an embodiment, the disclosed techniques can use image data and/or position data from the endoscope to track the endoscope's global movement in the global reference frame and update the patient frame from this information. This creates an actual ground truth of endoscope position inside the patient, whereas approaches using external sensors assume everything is accurately tied to a global coordinate system. In this manner, the movement of the patient can be disregarded, because the endoscope generates ground truth location and environment information within the patient. Thus, external patient movement sensors that provide patient position information spatially within a room (in a global reference frame external to the patient) over the course of the procedure may be eliminated from the system 10 in certain embodiments.

In an embodiment, the system 10 may perform an initial registration of the anatomy model 12 with the patient 40 by synchronizing the location of the simulated endoscope 24 and real world endoscope 30, such as by registering the simulated endoscope 24 at the lips of the model 12 when the real world endoscope 30 passes the patient's lips. In an embodiment, the anatomy model 12 is registered at least in part relative to one or more detectable exterior patient features resolvable by a camera, such as a detected nasal opening, lips, or shoulder of the patient. The initial registration provides a starting point for rendering the simulated endoscope 24 within the model 12 according to the actual position of the endoscope 30 within the patient 40.

Figure 3:
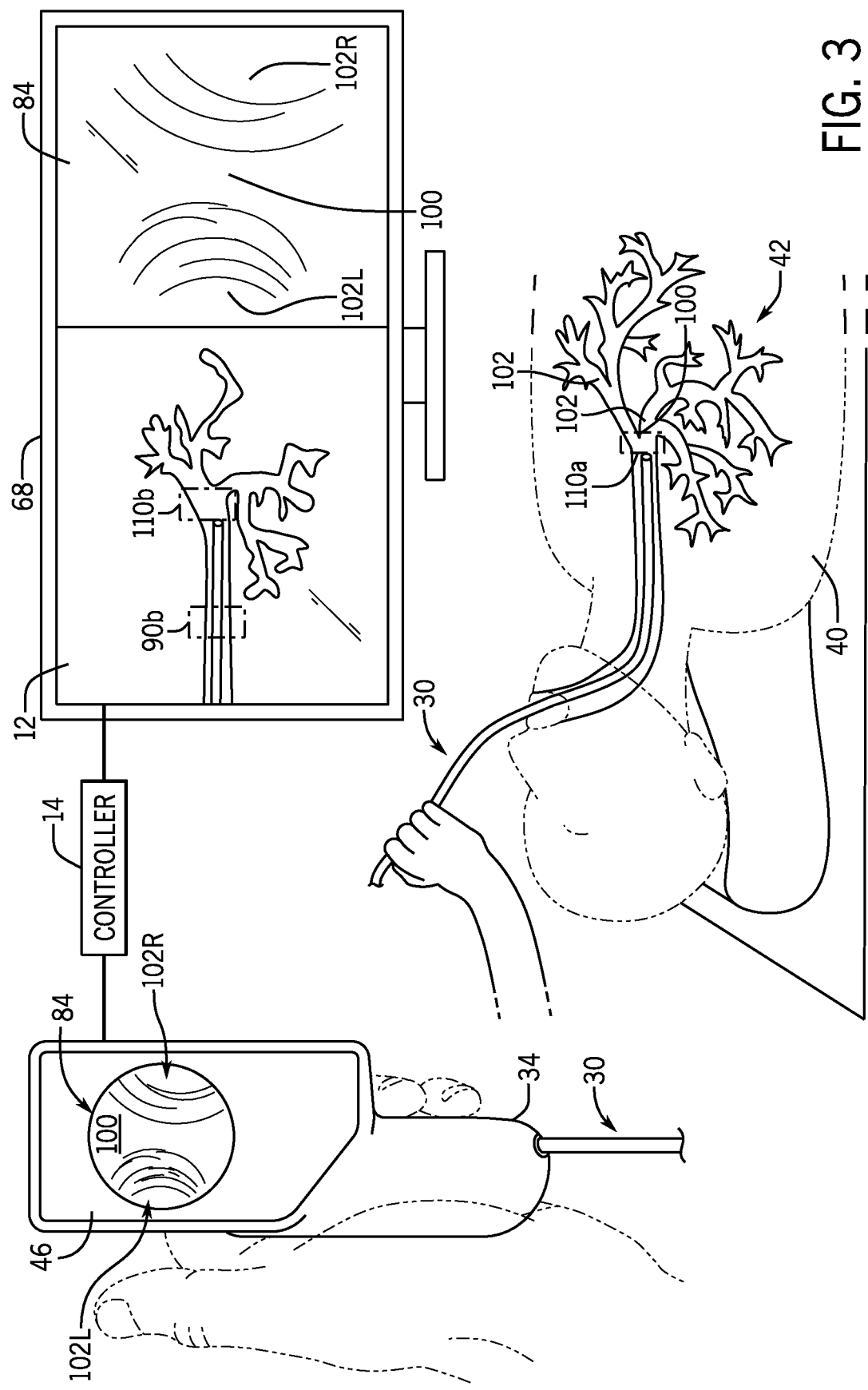
FIG. 3 is an endoscope navigation system including an endoscope view of a carina captured by the endoscope camera, according to an embodiment of the disclosure.

In FIG. 3, the endoscope operator has advanced the endoscope 30 distally, moving the endoscope 30 further forward into the patient airway, toward the carina 100. (The carina 100 is the tissue at the end of the trachea, where the trachea divides into the left and right bronchial tubes 102L, 102R.) FIG. 3 includes a cut-away front view of the endoscope controller 34, showing the front of the operator display screen 46. The operator display screen 46 shows the same camera image 84 as is displayed on the display screen 68. In this case, the image 84 shows the carina 100, left bronchial tube 102L, and right bronchial tube 102R. As shown in the anatomy model 12 FIG. 3, the simulated endoscope 24 has moved forward distally within the anatomy model 38, toward the carina 100. The carina 100 and the left and right bronchial tubes 102L, 102R of the anatomy model 12 are now within the field of view of the camera in a region 110a in the patient anatomy correlated to a region 110b in the model. The region 90b represents a previously viewed, corrected, or updated region of the anatomy model 12.

Figure 4:
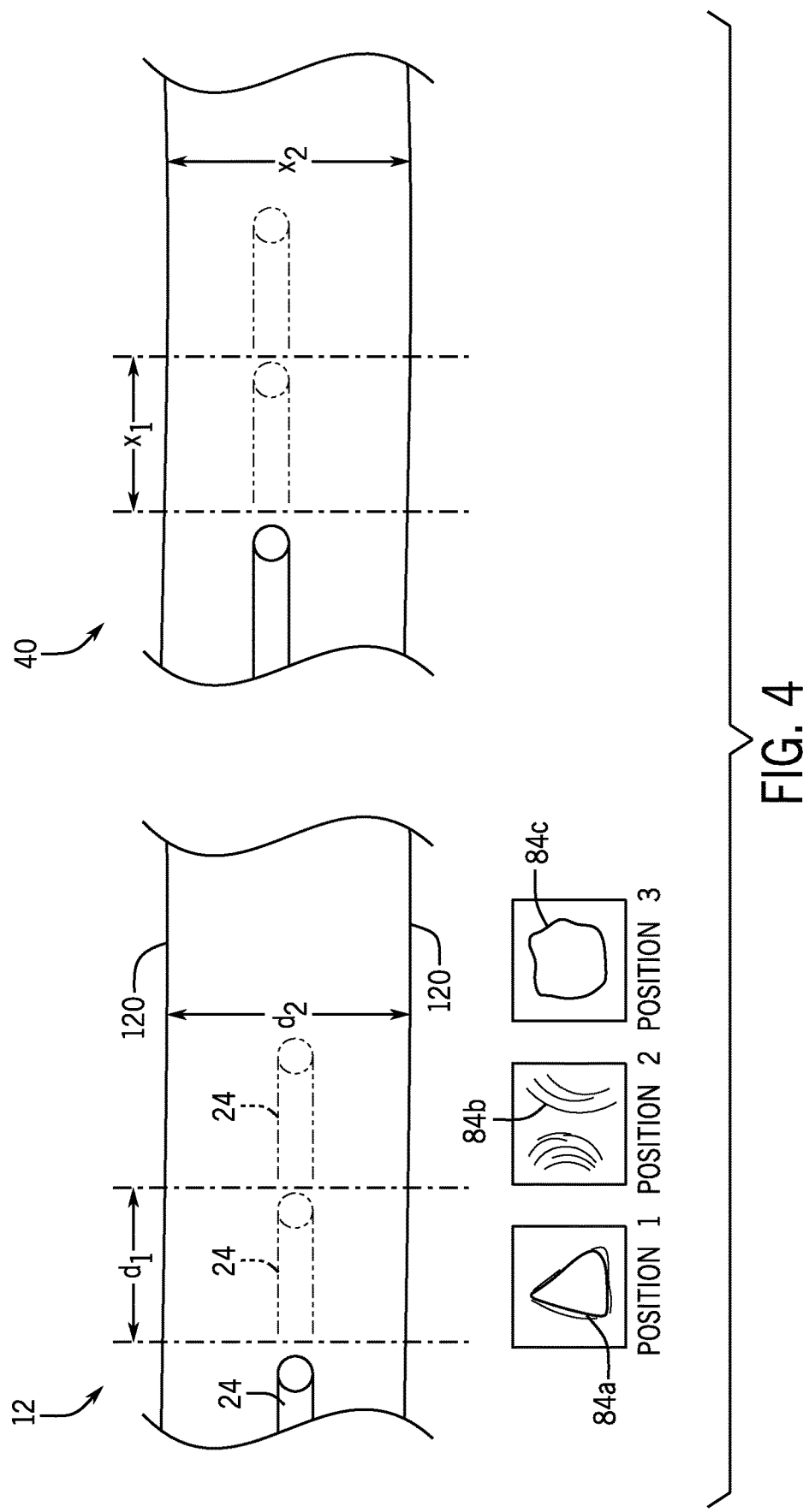
FIG. 4 is a view showing example anatomy model updating, according to an embodiment of the disclosure.
Figure 5:
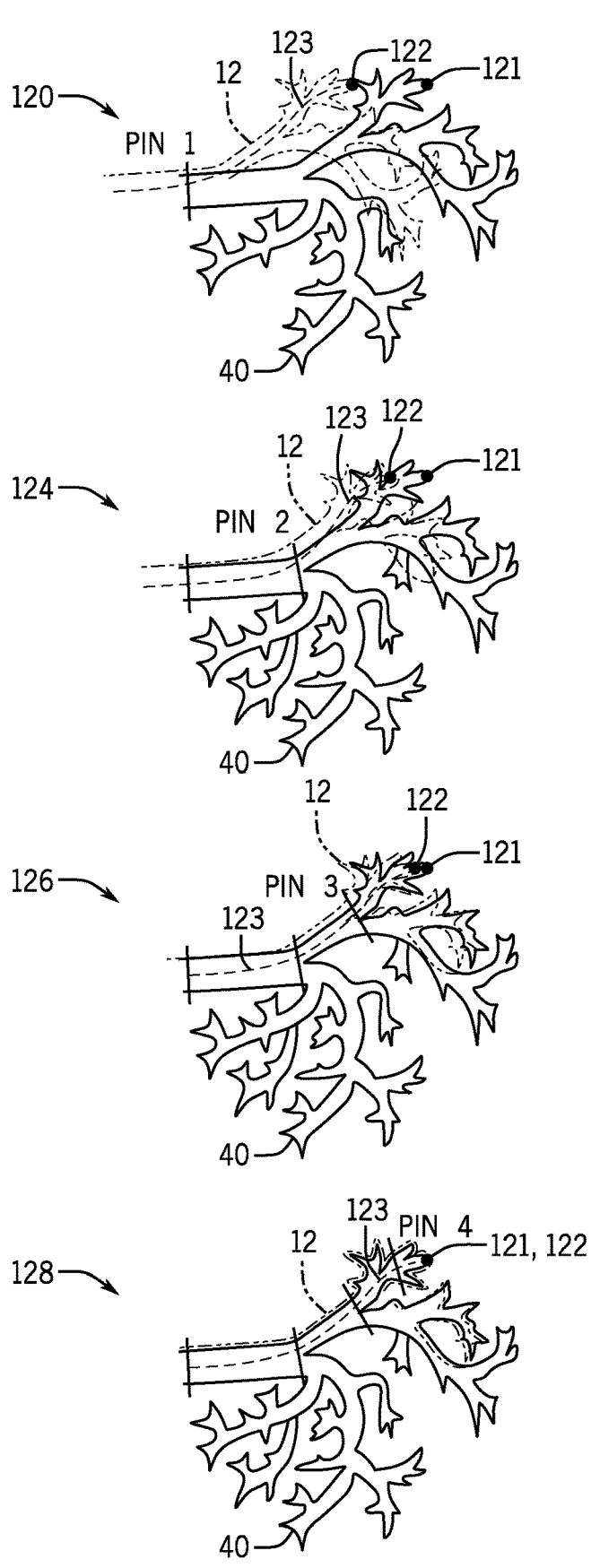
FIG. 5 shows example iterative anatomy model updating during endoscope progression to improve navigation over the course of a procedure, according to an embodiment of the disclosure.

FIGS. 4-6 are examples of adjustments to the anatomy model 12 based on identified divergences using live image signals. As provided herein, the system performs image processing of the live image signals to identify divergences between features in the images and corresponding features of the anatomy model 12. In certain embodiments, the real-time data may be used to adjust or correct the anatomy model 12 where there is a divergence between the anatomy model 12 and the real-time data. The updating may be according to a rules-based system, where the anatomy model 12 is adjusted with real-time data that (i) shows a divergence of a sufficient degree to perform an adjustment (such as a divergence of a certain threshold size, type, or other standard) and (ii) is determined to be reliable (such as by meeting quality criteria). In an embodiment, a divergence (between the real-time data and the model 12) may be sufficient to perform an adjustment if it shows a structural discrepancy between the model and the patient's anatomy, such as an airway passage at a different location or different size. In one embodiment, the real-time data is automatically deferred to as ground truth data. Thus, divergence between the real-time data and the model 12 is resolved in favor of the real-time data.

FIG. 4 shows adjustment of the anatomy model 12 based on an image signal including live images 84a, 84b, 84c at respective different positions 1, 2, and 3 in the patient. In one example, the movement of endoscope 30 between positions 1, 2, and 3 can be used to determine an actual distance x1 traveled by the endoscope 30 between those positions. The actual distance x1 can be compared to the corresponding distance d1 in the model 12 to determine that the anatomy model diverges from the live patient. The model 12 can then be adjusted to match the patient, such as by stretching or compressing distance d1 to match the distance x1. In one example, anatomical features in the first image 84a (e.g., vocal cords) and in the second image 84b (e.g., the carina) are identified via image processing and the actual distance between them is determined from the position difference between position 1 and position 2. These features are mapped to the model 12. If the distance between the features in the model (e.g., the distance between the vocal cords and the carina) diverges from the actual distance traveled by the endoscope (determined from position data from the endoscope), the model 12 is corrected. In another example, a passage diameter in the patient, shown as x2, can be calculated from the actual dimension of the passage using the captured live image 84c. If the actual dimension x2 of the patient 40 diverges from the corresponding dimension d2 of the model 12, the model 12 is changed to match the actual dimension (such as by expanding the diameter d2 of the modeled branch). In another example, a vector of one or more passages can be adjusted, with the distal passage anatomy approximated from these updates such that the simulated endoscope 24 relative to specific structures is more accurately rendered.

FIG. 5 shows steps in correcting the anatomy model 12 in real-time by pinning points of the model 12 at the branches (or other landmarks) where the model 12 is updated at each pin point to match the live patient 40. In FIG. 5, the model 12 is overlaid on the anatomy of the patient 40 in dashed lines for illustrative purposes to show the increasing conformance of a portion of the model 12 to the patient 40 after each step. At a first navigation step 120, the model 12 is shown veering off from the patient. Accordingly, navigation to a destination, shown by way of example as polyp 121, would be inaccurate if based only on the uncorrected model 12. However, as the endoscope progresses within the patient through successive navigation steps (steps 120, 124, 126, 128), the live endoscope data is used to correct the model 12 using the data at successive points (shown as pins 1, 2, 3, 4). As the model 12 is stretched, compressed, shifted, or otherwise redimensioned based on the image and position data at each pin, the model 12 starts to line up with the patient 40 more and more until the endoscope reaches the polyp 121 at the end, and the model 12 has updated in real-time to navigate correctly.

FIG. 5 illustrates the approach in which the previously acquired model 12 is updated in real-time based on live image data from the patient during a procedure. The model 12 shows a suggested navigation path 123 to the desired navigation target 122 within the model 12. The operator uses this path 123 to guide navigation of the actual endoscope 30 within the patient, acquiring live image and position data from within the patient. This live image and position data is fed back into the model 12 to update the model 12 and thus the modeled navigation path 123. The result is effectively a closed-loop navigation model in which the operator uses the model 12 to navigate within the patient and obtain live images, which are used to update the model 12 to assist further navigation. Further navigation results in more live images which are used to update the model 12 for further navigation. The model 12 is continually refined during the live procedure, so that the suggested navigation path 123 and navigation target 122 converges toward the actual destination, e.g., the polyp 121, of the target tissue within the patient.

As a result of the real-time correction, each next step is highly accurate, even if the entire path ahead is not. For example, at the first stage, based on the local data around pin 1, the model 12 conforms generally to the patient in the local area, even though the path ahead is still relatively inaccurate as shown by the divergence between the patient 40 and the model 12 in the illustration. As the endoscope moves to pin 2 at the next step 124, the system 10 receives more data that corrects the model in the local area around pin 2 to correct the position and angle of the modeled passageway. Again, the model 12 still diverges from the patient 40 at the next step 124, but the level of divergence decreases at each step. At a navigation endpoint step 128, there is minimal divergence between the model 12 and the patient 40 at least in the portion of the model 12 relevant to the navigation to the polyp 121. Further, the model 12 is sufficiently corrected to permit visualization of the polyp 121 and navigation past pin 4 using the live camera data. The real-time correction to the local data prevents confusion for the operator, because the live camera view will generally conform to the local area of the model 12. Thus, if the operator sees a passage bifurcation in the live camera view, the passage bifurcation is also present in the area of the model 12 around the simulated endoscope.

FIG. 5 shows iterative adjustment of the model 12 during endoscope navigation within a particular branch of the airway and based on local data acquired by the endoscope 30. However, the adjustments made based on the acquired local data may cause improved accuracy across the entire model 12. For example, the model 12 shows improved alignment with the patient anatomy over time, even in areas that correspond to branches not navigated by the endoscope 30.

The iterative adjustment to the model 12 of FIG. 5 may be part of a closed-loop navigation through an anatomy model 12. The closed-loop navigation may include rendering a simulated endoscope (e.g., a position marker) in the anatomy model 12 at location corresponding to a distal end of the endoscope 30. The closed-loop navigation may also include displaying a navigation path from the simulated endoscope to a target location. Movement of the endoscope 30 is tracked via a received position signal from the endoscope 30, and the simulated endoscope is moved in the anatomy model 12 according to the tracked movement, e.g., along the displayed navigation path. Any identified divergence between the anatomy model 12 and the received image data from the endoscope 30 can be used to update the model 12 in a closed-loop manner. The displayed navigation path and, in embodiments, the simulated endoscope are displayed in the updated anatomy model 12.

Figure 6A:
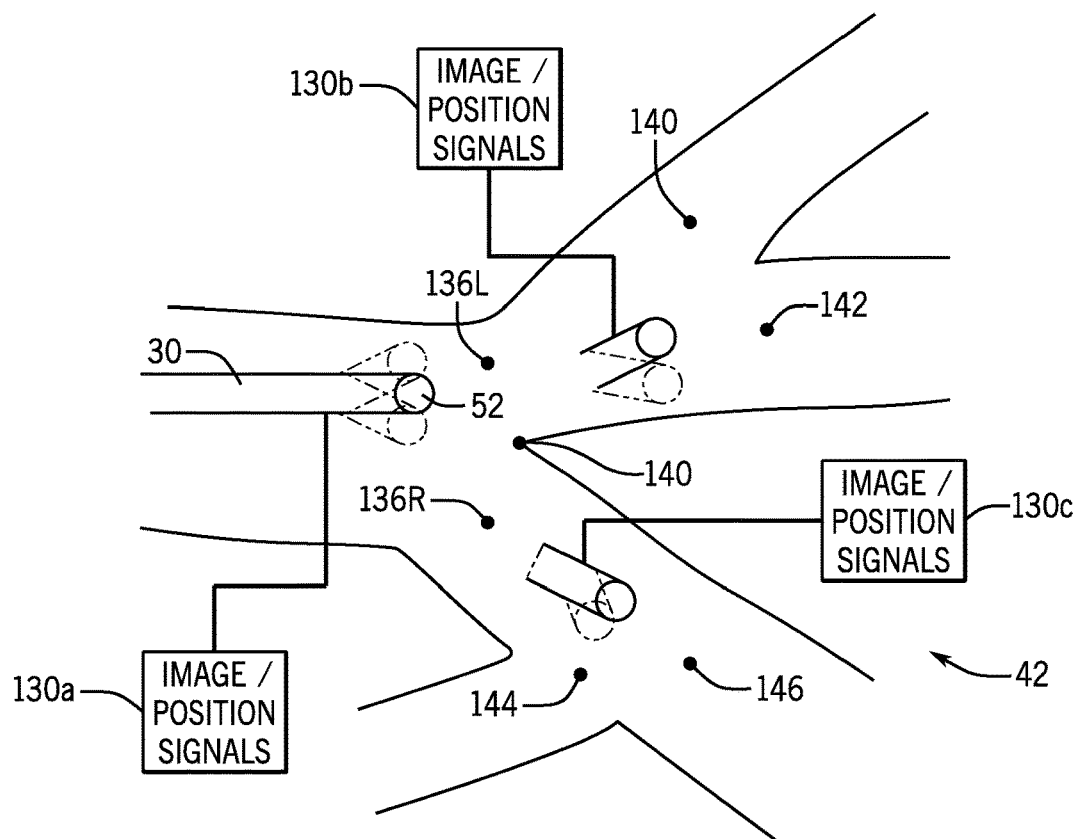
FIG. 6A is a view showing locations of image signals acquired during steering within the patient anatomy and used for anatomy model updating, according to an embodiment of the disclosure.

FIG. 6A shows an example of landmark recognition from endoscope signals 130. Landmark recognition may involve image processing to identify features that are present in the signals 130 such as the vocal cords, bifurcations of passageways, or other anatomy landmarks However, in embodiments, landmarks may be identified based on operator input, e.g., via the touch screen. For example, the endoscope 30 acquires image data from the endoscope signal 130a in which a left bronchial opening 136L and a right bronchial opening 136R are visible. The bronchial openings, and the carina 140, can be identified from rules-based image processing. For example, the carina 140 is located at a proximal-most bifurcation of the bronchial tree distal of the vocal cords. After identification of the vocal cords, the carina 140 is likely to be located at the first bifurcation point distal of the vocal cords. Thus, any more distal bifurcation is unlikely to include the carina 140. Image features of the bifurcation include generally circular dark regions separated by a light region that joins an outer perimeter surrounding the dark regions. Openings or bifurcations 140, 142, 144, 146 within the left and right bronchial passages can follow similar rules based identification based on dark openings separated by a lighter region in the image, by way of example. Passage openings may be designated by dark areas having a lighter perimeter. Landmark recognition may be used to correct the model 12 as discussed herein. Unique landmarks, such as the vocal cords or carina (each patient has only one set of vocal cords or one carina), can be used to adjust the model 12 based on the corresponding unique structure and the relative position of the endoscope to the unique structure.

Figure 6B:
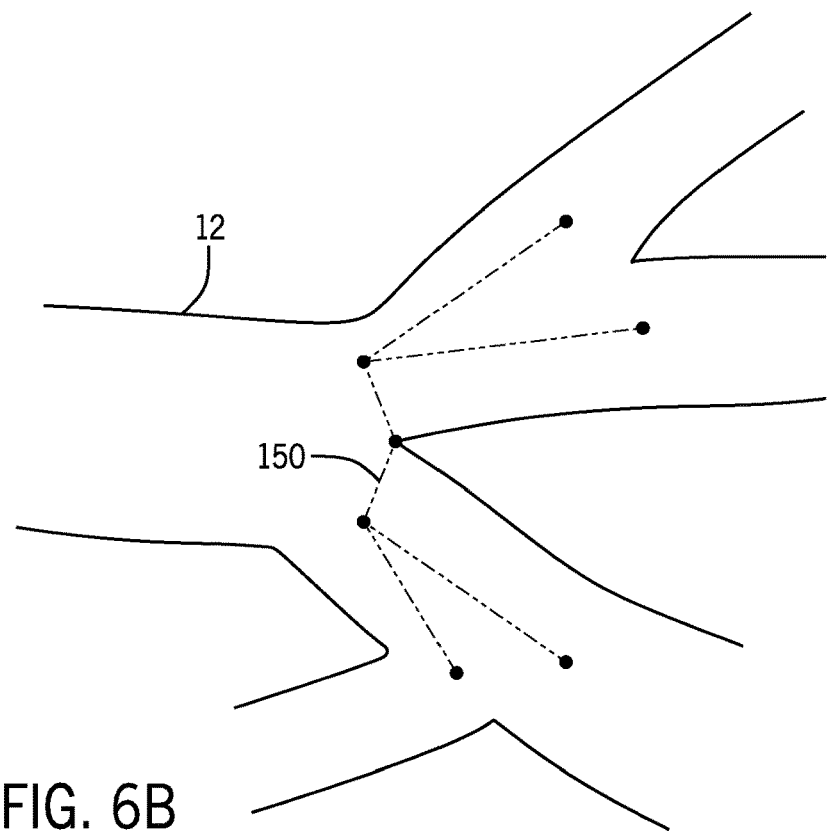
FIG. 6B is a view showing example anatomy model updating using the image signals of FIG. 6A, according to an embodiment of the disclosure.

In certain embodiments, the identified landmarks can be tied to positions in space based on the position data in the signals 130. In one example, as shown in FIG. 6B, two or more identified landmarks, and their absolute positions relative to one another can be used for adjustment of the model 12 to better conform to the patient anatomy. When the image data in the endoscope signal 130 is acquired with associated position data, the distances between each identified landmark in the image data can determined. The model 12 can be fit to conform to the relative positional arrangement of the identified landmarks. In the illustrated example, a positional arrangement 150 of seven different landmarks is shown, but more or fewer landmarks may also be used. The arrangement 150 can be based on distances traveled by the endoscope between different landmarks. These distances can be scaled according to a model scaling factor, and used to adjust features of the model 12. The model 12 can be adjusted by stretching or compressing different regions of the model 12 to fit to the fixed branch points in the arrangement 150. For example, use of absolute position data may be beneficial when considering operating areas (e.g., ablation areas, heating or cooling areas) of surgical tools visualized within the model 12.

FIG. 7 shows navigation in the patient's airway passages 42. Example growths may include peripheral nodules, lesions, polyps, scarring, or areas of bleeding. Panel A shows example uncorrected model (upper box) and patient physiology (low box). In the upper box of panel A, the example uncorrected model shows a suggested navigation path to a location 288a within the model to navigate the endoscope to a growth 288 in the patient anatomy. However, the uncorrected model does not conform to the patient, and this path appears as path B which is physically impossible to follow in the model. Path B goes "off-road" into an area outside the modeled physiology. Thus, displayed navigation of Path B is not helpful to the operator in finding the growth 288, and the operator has to guess where to go next in the live patient. In trying to follow the off-road path B, the operator may then navigate into an incorrect passage A (lower panel, prior art), which does not include the growth. Each wrong turn requires back-tracking and a new guess as to the correct path, which extends the procedure time.

Panel B, in contrast, shows navigation that corrects the model 12 in real-time based on live patient physiology images. The navigation requires navigation along path 190 to reach the actual growth 188, as shown in the lower box of Panel B. In the illustrated embodiment, the model 12a transitions to the updated model 12b over the course of the navigation as additional live endoscope data is captured. Thus, the displayed modeled (e.g., suggested path) navigation route 180 to the displayed destination 188b does not go "off-road" outside of the modeled physiology. By the time the endoscope 30 reaches the growth 188 in the patient anatomy, the model 12b has updated so that the displayed navigation 180 leads the operator through the correct path 190 in the live patient to the growth 188, which generally corresponds to the displayed navigation destination 188b. While FIG. 7 shows only a single transition between the models 12a, 12b, it should be understood that the updating can happen several times and at each new location of the endoscope 30.

Figure 8:
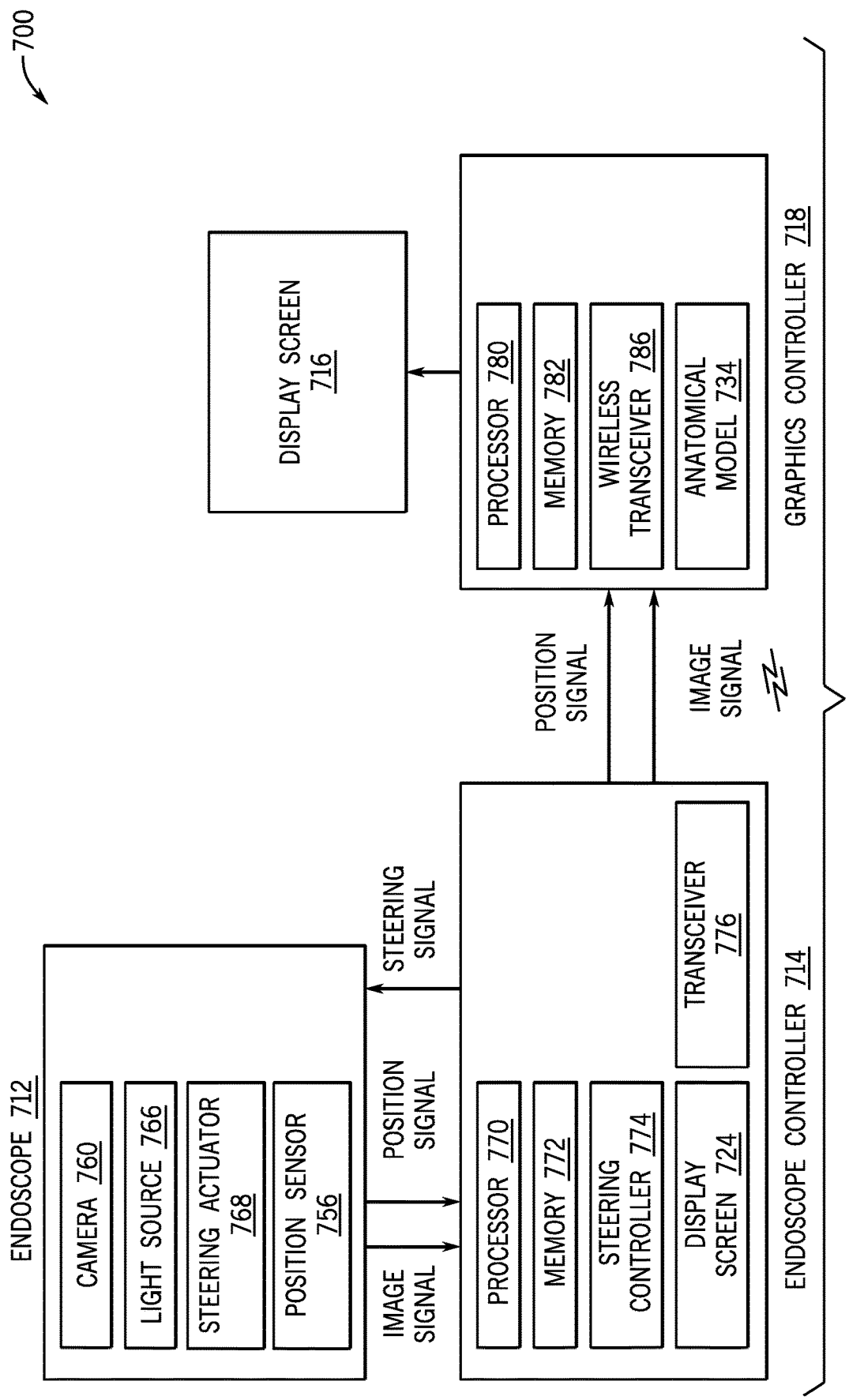
FIG. 8 is a schematic block diagram of an endoscope navigation system, according to an embodiment of the disclosure.

A block diagram of an endoscope navigation system 700 with an updating anatomy model is shown in FIG. 8, according to an embodiment. As shown, the system includes an endoscope 712, endoscope controller 714, graphics controller 718, and separate display 716. The endoscope 712 includes a camera 760, light source 766 (such as an LED shining forward from the distal tip of the endoscope), a steering actuator 768 (coupled to distal steerable segments of the endoscope, to bend or un-bend them as described below), and a position sensor 756. The endoscope 712 is connected by a wired (shown) or wireless connection to the endoscope controller 714, which includes a processor 770, hardware memory 772, steering controller 774 (such as a motor or other driver for operating the actuator 768), display screen 724, and wireless transceiver 776. The endoscope controller 714 is connected by a wired or wireless (shown) connection to the graphics controller 718, which also includes a processor 780, hardware memory 782, wireless transceiver 786, and the stored anatomy model 734. The graphics controller 718 may be, for example, a laptop or desktop computer running software stored on the memory 782. The graphics controller 718 is connected by a wired or wireless (shown) connection to the display 716. In an embodiment, the display 716 is a hardware display screen fixedly or portably mounted in an environment of the patient. In one embodiment, the display 716 may be an augmented reality viewer such as goggles or glasses that includes hardware components that display the anatomy model 734 overlaid on the patient.

In an embodiment, the endoscope 712 includes one, two, or more steerable segments at the distal end of the endoscope. Each steerable segment can articulate independently of the other segments. In an embodiment, each steerable segment can bend and curve in three dimensions (not just in a single plane, such as up/down or right/left), curving to points in all directions up to a limit of its range of motion. For example, in an embodiment each segment can bend up to 90 degrees in any direction, enabling it to move within a hemisphere having a radius equal to the segment's length. Each segment is manipulated by its own actuation system, including one or more actuators (such as sleeved pull-wires or other actuators described below), which moves to bend or un-bend the segment into or out of a curved or bent shape.

Each articulating segment at the distal end of the endoscope is manipulated by a steering system (such as steering controller 774), which operates an actuator (such as steering actuator 768) that is coupled to the segment to bend or straighten the segment. The steering system may include one or more memory metal components (e.g., memory wire, Nitinol wire) that changes shape based on electrical input, a piezoelectric actuators (such as the SQUIGGLE motor from New Scale Technologies, Victor NY), a retractable sheath (retractable to release a pre-formed curved component such as spring steel which regains its curved shape when released from the sheath), mechanical control wires (pull wires), hydraulic actuators, servo motors, or other means for bending, rotating, or turning the distal end or components at the distal end of the endoscope.

The block diagram of FIG. 8 shows the signal flow between the various devices. In an embodiment, the endoscope 712 sends a live image signal (from the camera 760) and a live position signal (from the position sensor 756) to the endoscope controller 714. The endoscope controller 714 receives the image signal and displays image data on the display screen 724. The endoscope controller 714 also forwards the image signal and the orientation signal to the controller 718, such as through the wireless transceivers on the two devices, and/or through wired connections and/or intermediary devices. The controller 718 receives the image signal and updated the anatomy model displayed on the display 716. The image signal may also be routed to other devices, processor, or servers, and for example may be displayed or stored on other display screens, or devices.

The controller 718 receives the position signal and uses that information to adjust 1) the anatomy model and 2) the rendering of the simulated endoscope in the anatomy model. The position sensor 756 is an electronic component that senses the position and orientation (such as orientation relative to gravity) and/or movement (acceleration) of the distal end of the endoscope. The position sensor 756 contains a sensor or a combination of sensors to accomplish this, such as accelerometers, magnetometers, and gyroscopes. The position sensor 756 may generate absolute position data of the endoscope distal end or position data relative to a fixed reference point. The position sensor 756 may be an inertial measurement unit (IMU). The position sensor 756 detects static orientation and dynamic movement of the distal tip of the endoscope and provides a signal indicating a change in the endoscope's orientation and/or a motion of the endoscope. The position sensor 756 sends this signal to the controller 718. The position sensor 756 is located inside the tubular housing of the endoscope 712. As shown in FIG. 1, in an embodiment, the orientation sensor is located very close to the terminus of the distal end of the endoscope, such as behind the camera, to enable the position sensor 756 to capture much of the full range of movement of the distal tip and camera. In an embodiment, the position sensor 756 is placed at a distal end of the first steerable portion, remote from the proximal end of the steerable portion, to place the orientation sensor away from the fulcrum of movement.

In an embodiment, the position sensor 756 generates a position signal with position coordinates and heading of the distal tip of the endoscope 712. The controller 718 uses this coordinate and heading information to adjust the anatomy model 734 and the simulated endoscope 24 (shown in FIG. 2). For example, when the real-world endoscope 712 is moved distally by a distance of 1 mm inside the patient, this change in position is reported by the position sensor 756 through the position signal. The new position coordinates are received by the controller 718, and the simulated endoscope 24 is moved forward (distally) by the same or proportional amount within the anatomy model 734. The new position is then rendered graphically in the display 716. The data signal from the position sensor 756 may be referred to as an orientation signal, movement signal, or position signal.

In an embodiment, the controller 718 uses the position signal and/or the image signal to adjust the anatomy model as disclosed herein. Data extracted from the image signal that corresponds to a particular real-world position inside the patient is compared to the anatomy model 734 at a corresponding position. The stored anatomy model 734 may include various features, such as passage dimensions, distances between anatomy features, a location of a branch opening, wall thicknesses, arrangement of branches relative to one another, and peripheral nodule locations and sizes. When the image signal is received, the 2D images in the image signal are processed using object or feature recognition, image segmentation, principal components analysis, and/or machine learning to extract features of interest. Each extracted feature can be compared to the corresponding feature in the model. A divergence can be identified based on a difference in dimensions, distances, or locations beyond a tolerance (e.g., more than a 3% difference) between the patient and the model.

The processors (such as 770, 780, 790) may be a chip, a processing chip, a processing board, a chipset, a microprocessor, or similar devices. The controllers 714, 718 and the display 716 may also include a user input (touch screen, buttons, switches). The controllers 714, 718 may also include a power source (e.g., an integral or removable battery) that provides power to one or more components of the controller, endoscope, or viewer as well as communications circuitry to facilitate wired or wireless communication with other devices. In one embodiment, the communications circuitry may include a transceiver that facilitates handshake communications with remote medical devices or full-screen monitors. The communications circuitry may provide the received images to additional monitors in real time.

The processor may include one or more application specific integrated circuits (ASICs), one or more general purpose processors, one or more controllers, FPGA, GPU, TPU, one or more programmable circuits, or any combination thereof. For example, the processor may also include or refer to control circuitry for the display screen. The memory may include volatile memory, such as random access memory (RAM), and/or non-volatile memory, such as read-only memory (ROM).

The anatomy model is updated by the graphics controller (e.g., controller 14, 718) as a result of receiving the live, real-time image signal and the live, real-time position signal. In one embodiment, the updating of the anatomy model may be in substantially real-time in response to receiving the live image signal and the live position signal. In an embodiment, the updating of the anatomy model may be during the clinical procedure that produces the camera signal and the position signal. The updating time may depend on the nature of changes to the anatomy model, and certain changes may be computationally faster than others. In one embodiment, a region of the anatomy model is updated while the endoscope is still in a location in the anatomy corresponding to the updated region. In another embodiment, the anatomy model is updated while the endoscope is still within the patient but after the distal tip has moved beyond (i.e., distally of) the updated region. The updating of the anatomy model may be iterative and to the level of the available data in the image signal. Where additional image data becomes available, the system 10 can further refine the anatomy model.

The updated anatomy model can be stored in a memory (e.g., memory 782 of the graphics controller 718) and retained as part of a patient electronic medical record.

Thus, the disclosed embodiments provide a novel and dynamic closed loop navigation technique that improves upon conventional static anatomy models. The system receives live feedback from the endoscope 30 during a clinical procedure, and the live feedback is fed to a pre-existing anatomy model to adjust, correct, or improve the model. The changes to the anatomy model are retained at each feedback step such that the model becomes more and more accurate over the course of the clinical procedure. The adjustment to the model occurs in the background, so that the operator can continue navigating within the patient, focusing on the immediate steps in the navigation pathway. The system adjusts the anatomy model in real time to align the image from the endoscope camera with the corresponding portion of the anatomy model. Thus, the operator can visually confirm that the anatomy model is generally correct based on the endoscope view, and this can improve the operator's overall confidence in the navigation system.

Figure 9:
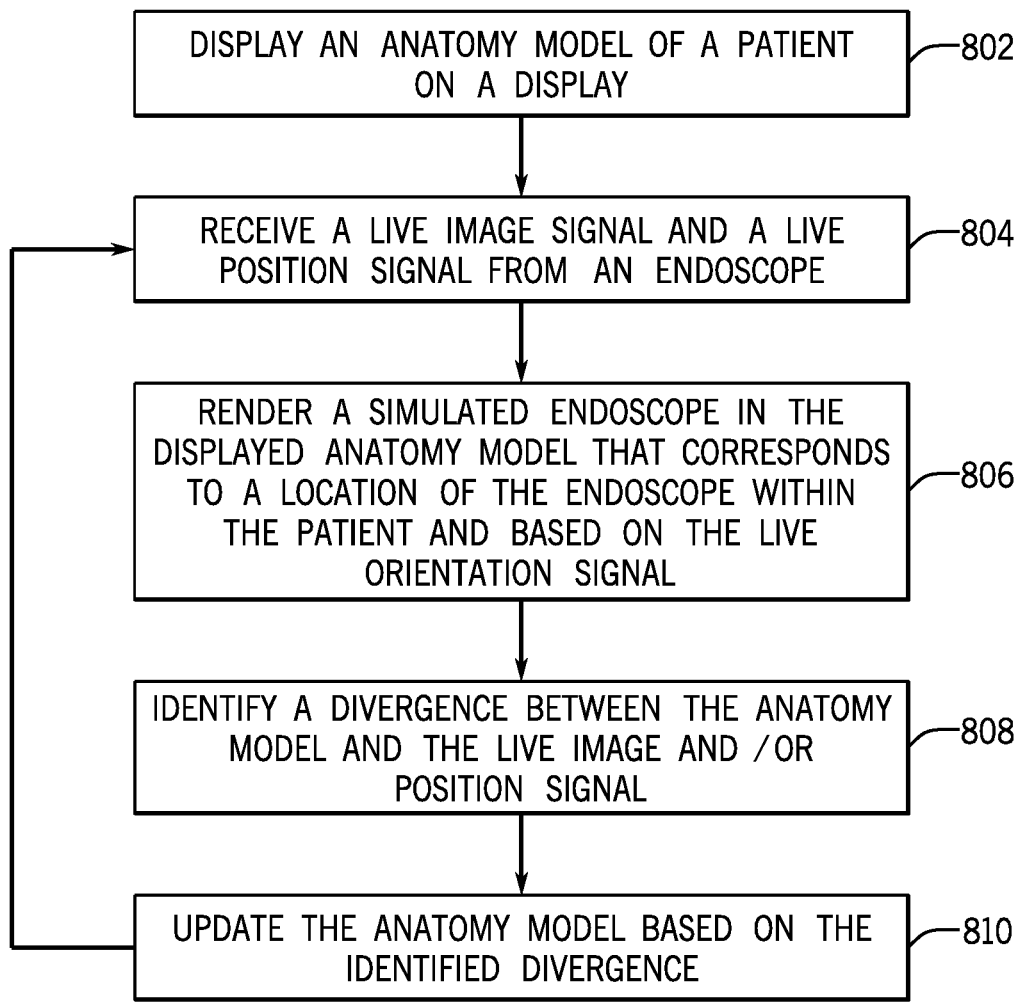
FIG. 9 is a flowchart of a method of updating an anatomy model during a procedure with an endoscope, according to an embodiment of the disclosure.

FIG. 9 is a flowchart depicting an endoscope navigation method 800 for updating an anatomy model during a procedure with an endoscope, according to an embodiment of the disclosure. The method includes displaying an anatomy model of a patient on a display, at 802. The anatomy model can be a baseline or initial anatomy model generated from patient scan data. The anatomy model can also be a previously adjusted or corrected anatomy model. The method also includes receiving, at a graphics controller, a live image signal and a live position signal from an endoscope, at 804. The method also includes a displaying graphical marker of a simulated endoscope in the anatomy model corresponding to a location of the endoscope within the patient, at 806. The method also includes identifying a divergence between the anatomy model and the live image signal, at 808, as generally disclosed herein. For example, the divergence can be identified as a divergence between the anatomy present in the live image signal and the anatomy present in the model at the location of the rendered endoscope. The method also includes updating the anatomy model or the rendering of the endoscope within the anatomy model based on the identified divergence, at 810. The method 800 can iterate back to receiving additional live image signals and live position signals, at 804, and continuing to update the anatomy model for successive identified divergences. In embodiments, the anatomy model may be generally determined to be generally accurate in particular regions in view of the live image and position data. In such cases, the regions in the anatomy model can be unaltered.

In one embodiment, based on the determination that a particular region is accurate, the anatomy model can be updated by indicating that the particular region is validated. For example, the region can be determined to be accurate after updating. In another example, the region can be determined to be accurate when any divergences are below threshold tolerances. The updated anatomy model can be stored in a memory of the system and, in embodiments, is provided to a display.

Figure 10:
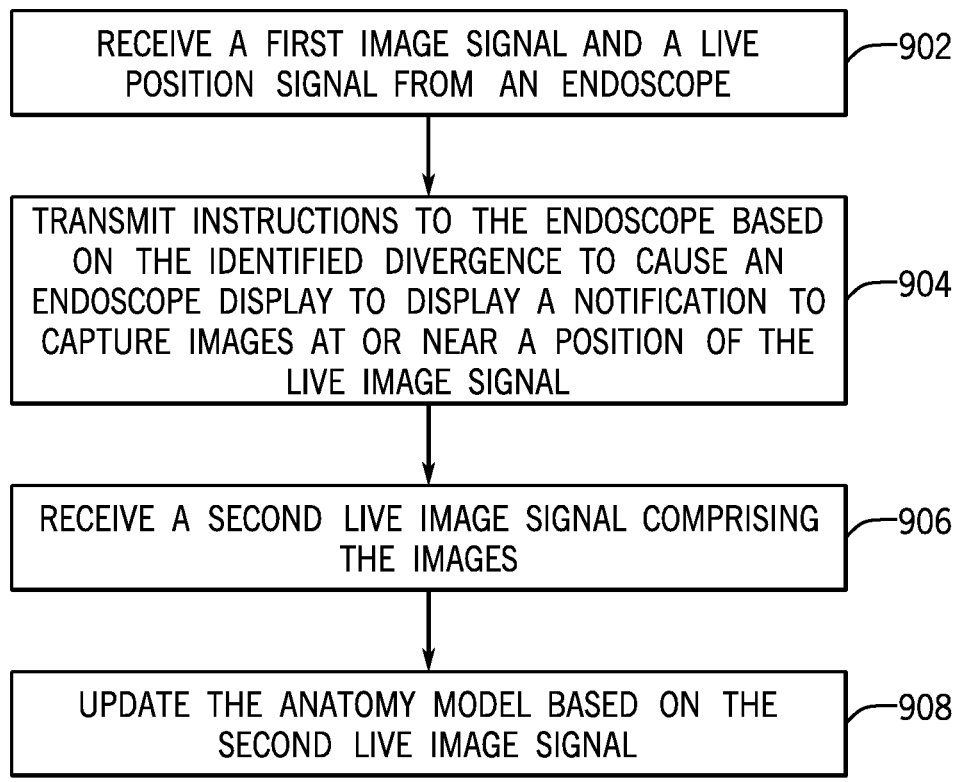
FIG. 10 is a flowchart of a method of updating an anatomy model during a procedure with an endoscope, according to an embodiment of the disclosure.

FIG. 10 is a flowchart depicting an endoscope navigation method 900 for updating an anatomy model during a procedure with an endoscope, according to an embodiment of the disclosure. The method includes receiving, at a graphics controller, a live image signal and a live position signal from an endoscope, at 902. The position signal includes position, orientation, and/or movement data from the position sensor of the endoscope, and the image signal includes 2D image data from the camera of the endoscope. In certain cases, the image quality may be poor, or the controller may not have enough data to determine if the anatomy model is accurate for the portion corresponding to the position of the camera. If the controller requires additional images to update or validate a portion of the model associated with the position of the camera, the method also includes transmitting instructions to the endoscope to cause an endoscope display to display a notification or activate another indication (e.g., haptic, optical, audio) to capture additional images at or near a position of the live image signal, at 904. The operator may respond to the notification by steering the endoscope at or near the position to capture additional images that are provided in the live image signal, e.g., in a second live image signal, that are received at the controller, at 906. For example, the operator can steer the tip 360 degrees without changing a distal position to acquire more data. The acquired data is streamed to the controller. When the controller has sufficient data, the anatomy model is validated and/or updated, at 908, and the notification can be deactivated. If the operator chooses to ignore the notification and advance within the airway, the portion of the model can be indicated as a lower confidence region, or can be updated using the available image signal.

Figure 11:
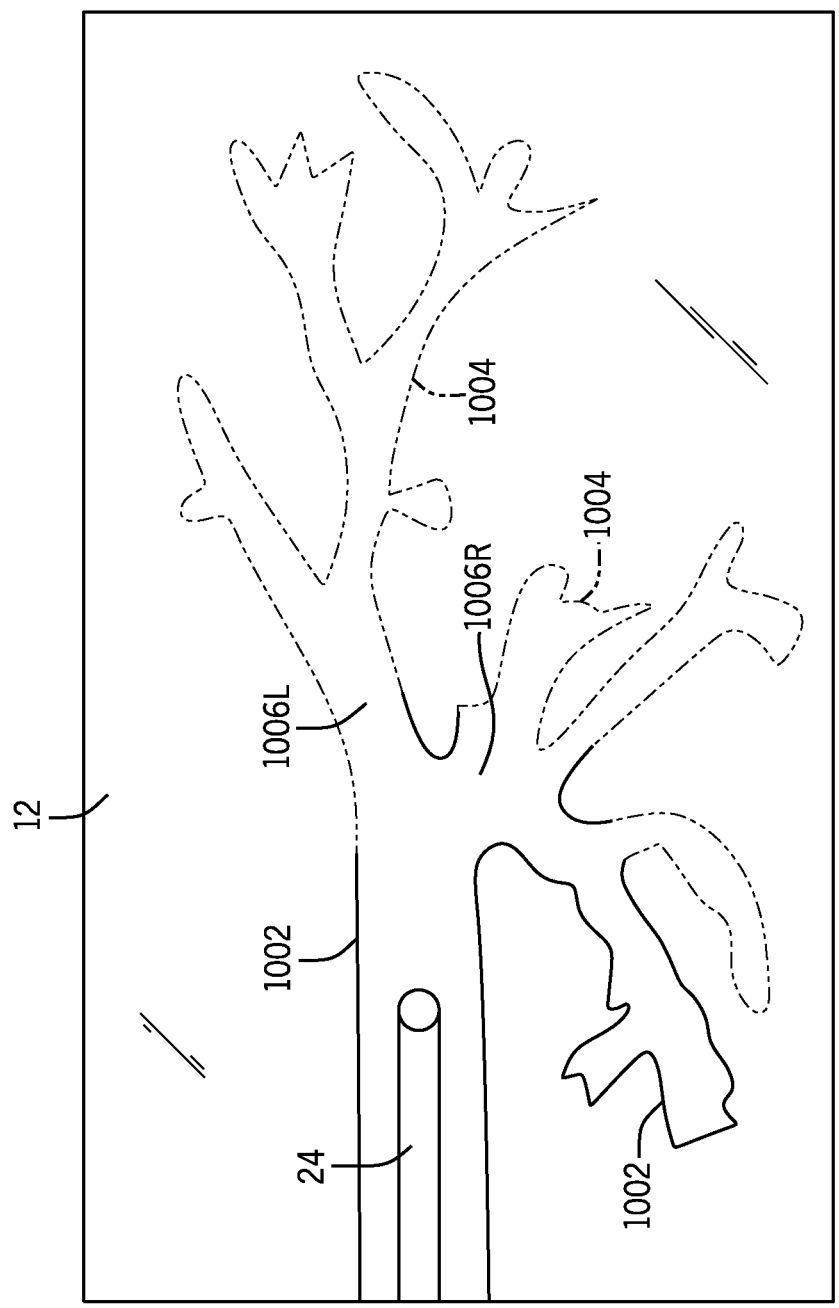
FIG. 11 is an example display of an anatomy model according to an embodiment of the disclosure.

The view of the updated anatomy model can take various shapes, colors, or forms. In an embodiment, the updating is generally not discernible in the displayed anatomy model 12, with updated or corrected model replacing the previous version. FIG. 11 is an example display of the anatomy model 12 that includes portions 1002, rendered in solid lines, that have been validated and/or adjusted and portions 1004, rendered in dashed lines, that have not been validated and/or adjusted. While the simulated endoscope 24 is shown in a position proximal of the left 1006L and right 1006R bronchial branches, the change in display characteristics of the model 12 can track previous movement of the endoscope 30. Accordingly, based on the solid versus dashed lines, the operator can visualize in the model 12 a previous pathway already navigated. The modification in display characteristics of the model 12 to show adjustment or validation of a portion of the initial anatomy model generated from the patient scan data may include shading the portion, changing a color of the portion, rending lines of the anatomy model in the portion in a different weight, or changing dashed lines to solid lines in the portion, by way of example. The modification may be relative to other unmodified portions that have not been validated and/or adjusted and that are based on the initial anatomy model 12.

While the present techniques are discussed in the context of endoscope navigation within airway passages, it should be understood that the disclosed techniques may also be useful in other types of airway management or clinical procedures. For example, the disclosed techniques may be used in conjunction with placement of other devices within the airway, secretion removal from an airway, arthroscopic surgery, bronchial visualization past the vocal cords (bronchoscopy), tube exchange, lung biopsy, nasal or nasotracheal intubation, etc. In certain embodiments, the disclosed visualization instruments may be used for visualization of anatomy (such as the pharynx, larynx, trachea, bronchial tubes, stomach, esophagus, upper and lower airway, ear-nose-throat, vocal cords), or biopsy of tumors, masses or tissues. The disclosed visualization instruments may also be used for or in conjunction with suctioning, drug delivery, ablation, or other treatments of visualized tissue and may also be used in conjunction with endoscopes, bougies, introducers, scopes, or probes. Further, the disclosed techniques may also be applied to navigation and/or patient visualization using other clinical techniques and/or instruments, such as patient catheterization techniques. By way of example, contemplated techniques include cystoscopy, cardiac catheterization, catheter ablation, catheter drug delivery, or catheter-based minimally invasive surgery.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. An endoscope navigation system, comprising:
   an endoscope comprising a steerable distal tip with a camera producing an image signal and with a position sensor producing a position signal indicative of a position of the steerable distal tip;
   a graphics controller programmed with instructions to:
      render a modeled navigation path in an anatomy model of a patient;
      receive the image signal and the position signal;
      based on at least the position signal, determine an initial position of the distal tip of the endoscope within the anatomy model;
      identify a divergence between the anatomy model and an anatomical feature detected based on at least one of the image signal or the position signal; and
      update the initial position of the distal tip of the endoscope in the anatomy model based on the identified divergence to reflect a current physical position of the distal tip of the endoscope; and
   a display screen displaying the updated position of the distal tip in the anatomy model.

2. The system of claim 1, wherein the display screen displays the anatomy model and an image from the image signal.

3. The system of claim 1, wherein the graphics controller is further programmed with instructions to update the anatomy model based on the divergence, wherein the updated anatomy model comprises an updated modeled navigation path.

4. The system of claim 1, wherein the graphics controller is further programmed with instructions to update the anatomy model, based on the divergence, by stretching or scaling the anatomy model.

5. The system of claim 1, wherein displaying the updated position of the distal tip in the anatomy model includes displaying a simulated endoscope rendered in the anatomy model according to the updated position of the steerable distal tip.

6. The system of claim 5, wherein the graphics controller updates the initial position of the distal tip in the anatomy model by identifying the anatomical feature in the image signal and aligning the simulated endoscope to a portion of the anatomy model corresponding to the identified anatomical feature.

7. The system of claim 1, wherein the graphics controller:
   correlates the position of the steerable distal tip to a correlated location in the anatomy model;
   extracts feature data from the image signal acquired at the position; and
   identifies the divergence based on a difference between the extracted feature data and the anatomy model at the correlated location.

8. The system of claim 7, wherein the difference is a dimension of an airway passage.

9. The system of claim 1, wherein the graphics controller is further programmed with instructions to update only a portion of the anatomy model based on the divergence.

10. The system of claim 1, wherein the anatomy model is based on previously acquired computer tomography images or magnetic resonance imaging.

11. An endoscope navigation method, comprising:
   displaying an anatomy model of a patient on a display screen;
   receiving an image signal and a position signal from an endoscope, the position signal indicative of a position of a distal tip of the endoscope during navigation;
   based on at least the position signal, determine an initial position of the distal tip of the endoscope within the anatomy model;
   rendering a graphical marker at a location in the displayed anatomy model that corresponds to the initial position of the distal tip;

identifying a divergence between an anatomical feature detected in the image signal and the location of the graphical marker in the anatomy model; and updating the location of the graphical marker in the displayed anatomy model based on the identified divergence to reflect a current physical position of the distal tip of the endoscope.

12. The method of claim 11, further comprising updating the anatomy model, based on the divergence, by adjusting a dimension of a passage or a position of a passage opening in the anatomy model.

13. The method of claim 11, further comprising updating the anatomy model, based on the divergence, by adding a nodule or tissue irregularity to the anatomy model or changing a location of the nodule or tissue irregularity in the anatomy model.

14. The method of claim 13, further comprising rerouting a navigation marker displayed on the anatomy model based on the changed location.

15. The method of claim 11, wherein the position signal is received from a position sensor located in a distal tip of the endoscope, and the position sensor includes at least one of an accelerometer, a magnetometer, or a gyroscope.

16. The method of claim 11, further comprising validating a portion of the anatomy model based on the updating and changing one or more display features of the validated portion in the displayed anatomy model.

17. The method of claim 11, wherein the updating is in substantially real-time.

18. The method of claim 11, wherein the anatomy model comprises a three-dimensional model of airway passages.

* * * * *